US011344886B2

(12) United States Patent
Raghunathan et al.

(10) Patent No.: US 11,344,886 B2
(45) Date of Patent: May 31, 2022

(54) MICROFLUIDIC DEVICE WITH CONSTANT HEATER UNIFORMITY

(71) Applicant: FluxErgy, LLC, Irvine, CA (US)

(72) Inventors: Ashwin Raghunathan, Santa Ana, CA (US); Steve Lee, Mission Viejo, CA (US); Ryan Alan Revilla, Costa Mesa, CA (US); Tej Rushikesh Patel, Carlsbad, CA (US)

(73) Assignee: FluxErgy, LLC, Irvine, CA (US)

( * ) Notice: Subject to any disclaimer, the term of this patent is extended or adjusted under 35 U.S.C. 154(b) by 167 days.

(21) Appl. No.: 16/751,782

(22) Filed: Jan. 24, 2020

(65) Prior Publication Data

US 2020/0238283 A1 Jul. 30, 2020

Related U.S. Application Data

(60) Provisional application No. 62/796,290, filed on Jan. 24, 2019.

(51) Int. Cl.

| | |
|---|---|
| ***B01L 3/00*** | (2006.01) |
| ***G01N 35/00*** | (2006.01) |
| ***G01N 15/06*** | (2006.01) |
| ***G01N 33/00*** | (2006.01) |
| ***G01N 33/48*** | (2006.01) |
| ***A61J 1/06*** | (2006.01) |
| ***B01L 7/00*** | (2006.01) |

(52) U.S. Cl.

CPC ... *B01L 3/502715* (2013.01); *B01L 3/502707* (2013.01); *B01L 7/52* (2013.01); *B01L 2200/12* (2013.01); *B01L 2300/0645* (2013.01); *B01L 2300/0816* (2013.01); *B01L 2300/12* (2013.01); *B01L 2300/1811* (2013.01)

(58) Field of Classification Search

CPC ......... B01L 2300/0816; B01L 2300/18; B01L 2300/0645; B01L 3/502715; B01L 7/52; B01L 3/00; G01N 35/00; G01N 15/06; G01N 33/00; G01N 33/48; A61J 1/06

See application file for complete search history.

(56) References Cited

U.S. PATENT DOCUMENTS

| | | | | |
|---|---|---|---|---|
| 10,272,437 | B2 * | 4/2019 | Kim | B01L 7/525 |
| 2009/0186404 | A1 * | 7/2009 | Kim | B01L 7/525 435/303.1 |
| 2017/0297029 | A1 * | 10/2017 | DeVoe | B01L 3/502707 |

OTHER PUBLICATIONS

Written Opinion of the International Preliminary Examining Authority for PCT/US2020/015023 dated Dec. 7, 2020—5 pages.

* cited by examiner

*Primary Examiner* — Brian J. Sines
(74) *Attorney, Agent, or Firm* — K&L Gates LLP

(57) ABSTRACT

A heater for a microfluidic test card is disclosed herein. In a general example embodiment, a test card for analyzing a fluid sample includes at least one substrate layer including a microchannel extending through at least a portion of one of the substrate layers, and a printed substrate layer that is bonded to or printed on one substrate layer of the at least one substrate layer. The printed substrate layer includes a heater printed on the printed substrate layer so as to align with at least a portion of the microchannel. The heater includes two electrodes aligned on opposite sides of the microchannel, and a plurality of heater bars electrically connecting the two electrodes. The plurality of heater bars includes a central heater bar disposed between outer heater bars.

10 Claims, 9 Drawing Sheets

MICROFLUIDIC DEVICE WITH CONSTANT HEATER UNIFORMITY

PRIORITY CLAIM

This application claims priority to and the benefit as a non-provisional application of U.S. Provisional Patent Application No. 62/796,290, filed Jan. 24, 2019, the entire contents of which are hereby incorporated by reference and relied upon.

CROSS-REFERENCE TO RELATED APPLICATIONS

This application is related to U.S. application Ser. No. 15/185,661, entitled "Test Card for Assay and Method of Manufacturing Same", filed Jun. 27, 2016, the entire contents of which is hereby incorporated by reference and relied upon.

FIELD OF THE DISCLOSURE

The present disclosure relates to a heater design for a microfluidic test card, and more specifically to a screen-printed heater design which can be used to perform a polymerase chain reaction ("PCR") within the test card.

BACKGROUND

Point-of-care ("POC") in vitro diagnostics tests ("IVDT") have traditionally had two major categories, nucleic acid amplification tests ("NAAT") or immunoassay-based tests. The former directly detects a pathogen's DNA or RNA, while the latter detects antibodies or antigens generated by a patient's (human or animal) immune system response to the pathogen.

Current POC diagnostic immunoassays lack the high sensitivity and specificity of nucleic acid amplification methods. This becomes more pronounced during the initial stages of infection, often within 168 hours. Taking the case of Dengue virus in whole blood, immunoglobulin M ("IgM") and immunoglobulin G ("IgG") remain undetectable in the majority of patients until 5 and 10 days post-infection, respectively, whereas nucleic acid can be found as early as 0 to 7 days. Moreover, many immunoassay tests are unable to detect infectious agents until 3 months after the initial onset of the infection. This delay is due to the time it takes for the body's immune system to respond to an infection.

POC diagnostic assays developed utilizing NAATs have very high sensitivities and specificities, matching those of currently accepted laboratory tests. The primary mechanism of NAAT based systems is to directly detect an infectious agent's nucleic acid, lending to the test's ability to detect diseases within the first few days of the onset of infection. In addition, by careful primer design, NAATs also have the ability to have very high specificity and sensitivity compared to immunoassay based testing. The largest drawback of NAATs compared to immunoassay-based tests is the complicated equipment and/or processes required to prepare a sample for testing.

Some known POC immunoassay testing systems analyze a patient sample during early stages of infection by causing a polymerase chain reaction ("PCR") within a test card. To cause the PCR, the patient sample has to be mixed with one or more reagents, such as a primer (e.g., oligonucleotides), a DNA polymerase, and/or a modified DNA polymerase. In addition, to cause the PCR, the reagent-patient sample mixture has to be heated on the test card. One issue that exists with test card screen-printed heaters is thermal uniformity, where a large temperature gradient results from a non-uniform current density. For example, a temperature gradient can be as large as 20 degrees over a 6 mm square area, which may cause major issues for PCR's, which require precise temperature control.

SUMMARY OF THE DISCLOSURE

Described herein is a screen-printed heater that is capable of uniformly raising a temperature of a fluid sample within a microchannel to cause a PCR. In a general example embodiment, which may be used in combination with any other embodiment disclosed herein, a test card for analyzing a fluid sample includes at least one substrate layer including a microchannel extending through at least a portion of one of the substrate layers, and a printed substrate layer that is bonded to or printed on one substrate layer of the at least one substrate layer. The printed substrate layer includes a heater printed on the printed substrate layer so as to align with at least a portion of the microchannel. The heater includes two electrodes aligned on opposite sides of the microchannel, and a plurality of heater bars electrically connecting the two electrodes. The plurality of heater bars includes a central heater bar disposed between outer heater bars. The central heater bar may be thinner than the outer heater bars in a direction approximately parallel to the microchannel.

In another embodiment, which may be used in combination with any other embodiment disclosed herein, the at least one substrate layer includes a plurality of bonded layers.

In another embodiment, which may be used in combination with any other embodiment disclosed herein, the electrodes are printed onto the printed substrate layer with a silver ink.

In another embodiment, which may be used in combination with any other embodiment disclosed herein, the plurality of heater bars is printed onto the printed substrate layer with a carbon ink.

In another embodiment, which may be used in combination with any other embodiment disclosed herein, the plurality of heater bars includes the central heater bar, a pair of first outer heater bars, and a pair of second outer heater bars, the central heater bar is disposed between the first outer heater bars, the first outer heater bars are disposed between the second outer heater bars, the central heater bar is thinner than the first outer heater bars in the direction approximately parallel to the microchannel, and the first outer heater bars are thinner than the second outer heater bars in the direction approximately parallel to the microchannel.

In another embodiment, which may be used in combination with any other embodiment disclosed herein, the central heater bar is thinner than the outer heater bars at a central point between the two electrodes.

In another embodiment, which may be used in combination with any other embodiment disclosed herein, the central heater bar is thinner than the outer heater bars at respective points of contact with at least one of the two electrodes.

In another embodiment, which may be used in combination with any other embodiment disclosed herein, the central heater bar is thinner than the outer heater bars at respective portions aligned with the microchannel.

In another embodiment, which may be used in combination with any other embodiment disclosed herein, the plurality of heater bars each includes a central diamond shape and two protruding ends, and the protruding ends overlap with the two electrodes to place the two electrodes in electrical communication with each other.

In a general embodiment, which may be used in combination with any other embodiment disclosed herein, a test card for analyzing a fluid sample includes at least one substrate layer including a microchannel extending through at least a portion of one of the substrate layers, and a printed substrate layer that is bonded to or printed on one substrate layer of the at least one substrate layer. The printed substrate layer includes a heater printed on the printed substrate layer so as to align with at least a portion of the microchannel. The heater includes two electrodes aligned on opposite sides of the microchannel, and a plurality of heater bars electrically connecting the two electrodes. The plurality of heater bars include a central heater bar disposed between outer heater bars, where the central heater bar has a higher resistance than the outer heater bars.

In another embodiment, which may be used in combination with any other embodiment disclosed herein, the at least one substrate layers includes a plurality of bonded layers.

In another embodiment, which may be used in combination with any other embodiment disclosed herein, the electrodes are printed onto the printed substrate layer with a silver ink.

In another embodiment, which may be used in combination with any other embodiment disclosed herein, the plurality of heater bars is printed onto the printed substrate layer with a carbon ink.

In another embodiment, which may be used in combination with any other embodiment disclosed herein, the plurality of heater bars includes the central heater bar, a pair of first outer heater bars, and a pair of second outer heater bars, the central heater bar is disposed between the first outer heater bars, the first outer heater bars are disposed between the second outer heater bars, the central heater bar is thinner than the first outer heater bars in a direction approximately parallel to the microchannel, and the first outer heater bars are thinner than the second outer heater bars in the direction approximately parallel to the microchannel.

In another embodiment, which may be used in combination with any other embodiment disclosed herein, the central heater bar is thinner than the outer heater bars at a central point between the two electrodes.

In another embodiment, which may be used in combination with any other embodiment disclosed herein, the central heater bar is thinner than the outer heater bars at respective points of contact with at least one of the two electrodes.

In another embodiment, which may be used in combination with any other embodiment disclosed herein, the central heater bar is thinner than the outer heater bars at respective portions aligned with the microchannel.

In another embodiment, which may be used in combination with any other embodiment disclosed herein, the plurality of heater bars each includes a central diamond shape and two protruding ends, and the protruding ends overlap with the two electrodes to place the two electrodes in electrical communication with each other.

In another general embodiment, which may be used in combination with any other embodiment disclosed herein, a heater for a substrate includes two electrodes spaced apart from each other in a first direction, and a plurality of heater bars connecting the two electrodes, the plurality of heater bars including a central heater bar disposed between outer heater bars, the central heater bar being thinner than the outer heater bars in a second direction approximately perpendicular to the first direction.

In another embodiment, which may be used in combination with any other embodiment disclosed herein, the outer heater bars are progressively thicker in the second direction as the distance from the central heater bar increases in the second direction.

In another embodiment, which may be used in combination with any other embodiment disclosed herein, the plurality of heater bars are each shaped to be thickest at a central point between the two electrodes in the first direction.

In another embodiment, which may be used in combination with any other embodiment disclosed herein, the electrodes are printed onto the substrate with a silver ink.

In another embodiment, which may be used in combination with any other embodiment disclosed herein, the plurality of heater bars is printed onto the substrate with a carbon ink.

In another embodiment, which may be used in combination with any other embodiment disclosed herein, the plurality of heater bars includes the central heater bar, a pair of first outer heater bars, and a pair of second outer heater bars, the central heater bar is disposed between the pair of first outer heater bars, the first outer heater bars are disposed between the second outer heater bars, the central heater bar is thinner than the first outer heater bars in the second direction, and the first outer heater bars are thinner than the second outer heater bars in the first direction.

In another embodiment, which may be used in combination with any other embodiment disclosed herein, the central heater bar is thinner than the outer heater bars at a central point between the two electrodes.

In another embodiment, which may be used in combination with any other embodiment disclosed herein, the central heater bar is thinner than the outer heater bars at respective points of contact with at least one of the two electrodes.

In another embodiment, which may be used in combination with any other embodiment disclosed herein, the heater is printed onto the substrate with conductive ink.

In another embodiment, which may be used in combination with any other embodiment disclosed herein, a heater for a substrate includes two electrodes spaced apart from each other in a first direction, and a plurality of heater bars connecting the two electrodes, the plurality of heater bars including a central heater bar disposed between outer heater bars, the central heater bar having a higher resistance than the outer heater bars.

In another embodiment, which may be used in combination with any other embodiment disclosed herein, the outer heater bars have progressively less resistance as the distance from the central heater bar increases in a second direction approximately perpendicular to the first direction.

In another embodiment, which may be used in combination with any other embodiment disclosed herein, the plurality of heater bars are each shaped to be thickest at a central point between the two electrodes.

In another embodiment, which may be used in combination with any other embodiment disclosed herein, the electrodes are printed onto the substrate with a silver ink.

In another embodiment, which may be used in combination with any other embodiment disclosed herein, the plurality of heater bars is printed onto the substrate with a carbon ink.

In another embodiment, which may be used in combination with any other embodiment disclosed herein, the plurality of heater bars includes the central heater bar, a pair of first outer heater bars, and a pair of second outer heater bars, the central heater bar is disposed between the first outer heater bars, the first outer heater bars are disposed between the second outer heater bars, the central heater bar is thinner than the first outer heater bars in a second direction approximately perpendicular to the first direction, and the first outer heater bars are thinner than the second outer heater bars in the second direction.

In another embodiment, which may be used in combination with any other embodiment disclosed herein, the central heater bar is thinner than the outer heater bars at a central point between the two electrodes.

In another embodiment, which may be used in combination with any other embodiment disclosed herein, the central heater bar is thinner than the outer heater bars at respective points of contact with at least one of the two electrodes.

In another embodiment, which may be used in combination with any other embodiment disclosed herein, the heater is printed onto the substrate with conductive ink.

In another general embodiment, which may be used in combination with any other embodiment disclosed herein, a method of providing a heater on a substrate includes printing two electrodes spaced apart from each other in a first direction, and printing a plurality of heater bars connecting the two electrodes, the plurality of heater bars including a central heater bar disposed between outer heater bars, the central heater bar being thinner than the outer heater bars in a second direction approximately perpendicular to the first direction.

In another embodiment, which may be used in combination with any other embodiment disclosed herein, the method includes printing the outer heater bars to be progressively thicker as the distance from the central heater bar increases in the second direction.

In another embodiment, which may be used in combination with any other embodiment disclosed herein, the method includes printing the plurality of heater bars to each be shaped to be thickest in the first direction at a central point between the two electrodes.

In another embodiment, which may be used in combination with any other embodiment disclosed herein, the method includes printing the electrodes onto the substrate with a silver ink.

In another embodiment, which may be used in combination with any other embodiment disclosed herein, the method includes printing the plurality of heater bars onto the substrate with a carbon ink.

In another embodiment, which may be used in combination with any other embodiment disclosed herein, the method includes printing the plurality of heater bars so as to include the central heater bar, a pair of first outer heater bars, and a pair of second outer heater bars, the central heater bar is disposed between the first outer heater bars, the first outer heater bars are disposed between the second outer heater bars, the central heater bar is thinner than the first outer heater bars in the second direction, and the first outer heater bars are thinner than the second outer heater bars in the second direction.

In another embodiment, which may be used in combination with any other embodiment disclosed herein, the method includes printing the central heater bar to be thinner than the outer heater bars at a central point between the two electrodes.

In another embodiment, which may be used in combination with any other embodiment disclosed herein, the method includes printing the central heater bar to be thinner than the outer heater bars at respective points of contact with at least one of the two electrodes.

In another embodiment, which may be used in combination with any other embodiment disclosed herein, the method includes printing the two electrodes and/or the plurality of heater bars onto the substrate with conductive ink.

In another embodiment, which may be used in combination with any other embodiment disclosed herein, the method includes printing the two electrodes so as to be aligned on opposite sides of a microchannel extending through at least a portion of the substrate.

In another embodiment, which may be used in combination with any other embodiment disclosed herein, the method includes printing the plurality of heater bars so as to overlap a microchannel extending through at least a portion of the substrate.

In another embodiment, which may be used in combination with any other embodiment disclosed herein, the method includes printing the plurality of heater bars so as to overlap the microchannel in a direction approximately perpendicular to the direction of the microchannel.

In another embodiment, which may be used in combination with any other embodiment disclosed herein, the method includes printing the plurality of heater bars before printing the two electrodes.

In another embodiment, which may be used in combination with any other embodiment disclosed herein, the method includes printing the two electrodes to at least partially overlap the plurality of heater bars.

In another general embodiment, which may be used in combination with any other embodiment disclosed herein, a method of providing a heater on a substrate includes printing two electrodes spaced apart from each other in a first direction, and printing a plurality of heater bars connecting the two electrodes, the plurality of heater bars including a central heater bar disposed between outer heater bars, the central heater bar having a higher resistance than the outer heater bars.

In another embodiment, which may be used in combination with any other embodiment disclosed herein, the method includes printing the outer heater bars to have progressively less resistance as the distance from the central heater bar increases in a second direction substantially perpendicular to the first direction.

In another embodiment, which may be used in combination with any other embodiment disclosed herein, the method includes printing the plurality of heater bars to each be shaped to be thickest at a central point between the two electrodes.

In another embodiment, which may be used in combination with any other embodiment disclosed herein, the method includes printing the electrodes onto the substrate with a silver ink.

In another embodiment, which may be used in combination with any other embodiment disclosed herein, the method includes printing the plurality of heater bars onto the substrate with a carbon ink.

In another embodiment, which may be used in combination with any other embodiment disclosed herein, the method includes printing the plurality of heater bars so as to include the central heater bar, a pair of first outer heater bars, and a pair of second outer heater bars, the central heater bar is disposed between the first outer heater bars, the first outer heater bars are disposed between the second outer heater bars, the central heater bar is thinner than the first outer heater bars in a second direction substantially perpendicular to the first direction, and the first outer heater bars are thinner than the second outer heater bars in the second direction.

In another embodiment, which may be used in combination with any other embodiment disclosed herein, the method includes printing the central heater bar to be thinner than the outer heater bars at a central point between the two electrodes.

In another embodiment, which may be used in combination with any other embodiment disclosed herein, the method includes printing the central heater bar to be thinner than the outer heater bars at respective points of contact with at least one of the two electrodes.

In another embodiment, which may be used in combination with any other embodiment disclosed herein, the method includes printing the two electrodes and/or the plurality of heater bars onto the substrate with conductive ink.

In another embodiment, which may be used in combination with any other embodiment disclosed herein, the method includes printing the two electrodes so as to be aligned on opposite sides of a microchannel extending through at least a portion of the substrate.

In another embodiment, which may be used in combination with any other embodiment disclosed herein, the method includes printing the plurality of heater bars so as to overlap a microchannel extending through at least a portion of the substrate.

In another embodiment, which may be used in combination with any other embodiment disclosed herein, the method includes printing the plurality of heater bars so as to overlap the microchannel in a direction approximately perpendicular to the direction of the microchannel.

In another embodiment, which may be used in combination with any other embodiment disclosed herein, the method includes printing the plurality of heater bars before printing the two electrodes.

In another embodiment, which may be used in combination with any other embodiment disclosed herein, the method includes printing the two electrodes to at least partially overlap the plurality of heater bars.

BRIEF DESCRIPTION OF THE DRAWINGS

Embodiments of the present disclosure will now be explained in further detail by way of example only with reference to the accompanying figures, in which.

DETAILED DESCRIPTION

Before describing in detail the illustrative system and method of the present disclosure, it should be understood and appreciated herein that the present disclosure relates to a test card for use with a rapid, high sensitivity and high specificity, low complexity diagnostic system using nucleic acid amplification and capable of operating in low resource settings with minimal user training. The system is configured, for example, to cause and analyze a polymerase chain reaction ("PCR") within the test card, particularly in the early stages of infection, using a low-cost microfluidic platform employing PCR with a modified DNA polymerase. In an embodiment, the test card is configured to receive about 10 μL of whole blood, the equivalent to a drop of blood obtained from a finger stick. In another embodiment, the fluid sample can be serum, urine, saliva, tears and/or the like.

Figure 1:
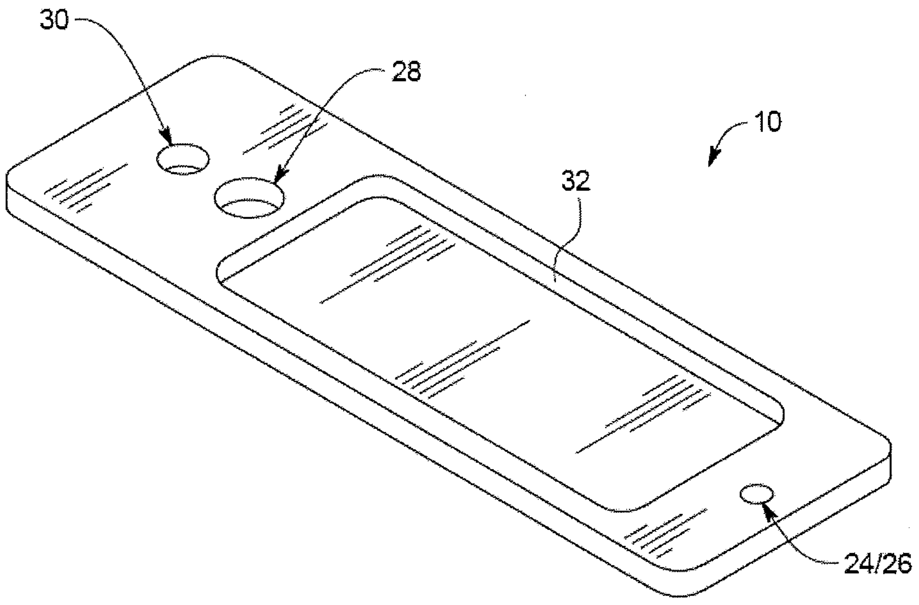
FIG. 1 is a top perspective view of an example embodiment of a test card, according to an example embodiment of the present disclosure.
Figure 2:
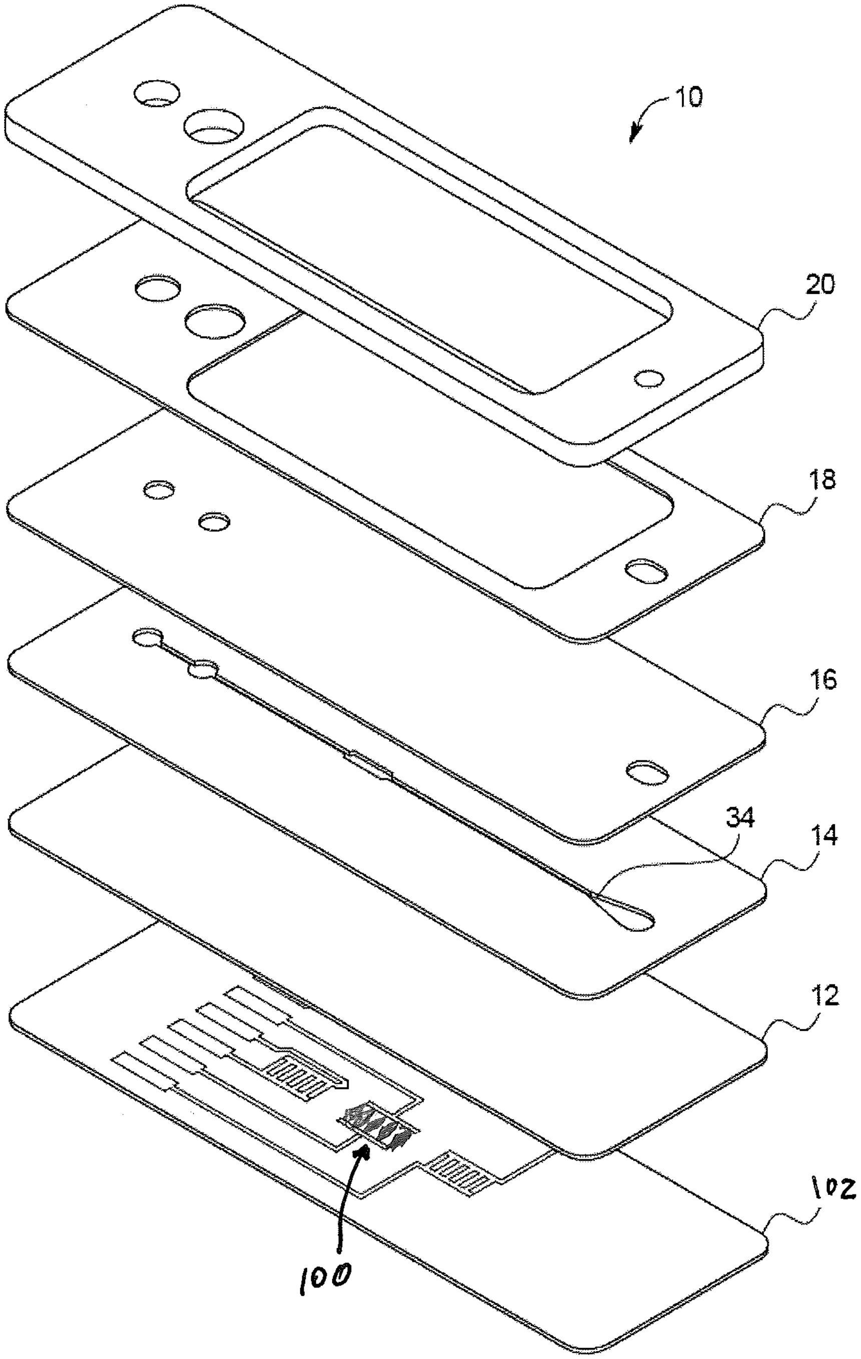
FIG. 2 is an exploded view of the test card of FIG. 1, according to an example embodiment of the present disclosure.
Figure 3:
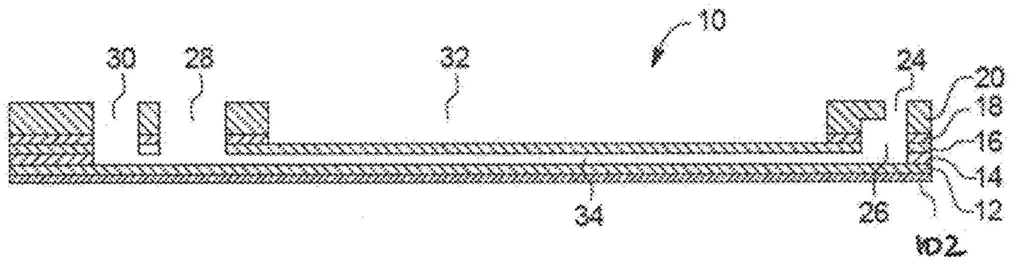
FIG. 3 is a cross-sectional view of the test card of FIG. 1, according to an example embodiment of the present disclosure.

FIGS. 1 to 3 illustrate an example embodiment of a test card 10 according to the present disclosure. As illustrated, test card 10 includes an inlet port 24/mixing chamber 26, a capture port 28, an outlet port 30, and a fluid microchannel 34. In use, a fluid sample can be placed into inlet port 24, mixed with one or more reagent in mixing chamber 26, and then pulled though fluid microchannel 34, so that the fluid sample can be analyzed through an analysis port 32 while residing within fluid microchannel 34 as a PCR occurs, in part, due to heat applied from a heater 100, according to the present disclosure.

In an embodiment, a vacuum source can be applied to the outlet port 30. When a negative pressure is applied to the outlet port 30, the vacuum pressure pulls the fluid sample from the mixing chamber 26 through fluid microchannel 34 so that the fluid sample can be analyzed through analysis port 32 while residing within a target zone of the microchannel 34. The capture port 28 is configured to capture fluid from the fluid sample before the fluid flows to the outlet port 30. In the illustrated embodiment, the capture port 28 is sized to allow fluid to build up before it can reach the outlet port 30 to prevent the fluid from being sucked out of the outlet port 30 by the vacuum pressure applied to the outlet port 30. In an embodiment, the capture port 28 can include a porous material, which can act like a sponge to absorb any excess fluid and prevent fluid from escaping from test card 10 due to mishandling.

As illustrated in FIGS. 2 and 3, the test card 10 may include one or more substrate layers including a bottom substrate layer 12, a channel layer 14, a middle substrate layer 16, an adhesive layer 18, a top substrate layer 20, and a printed circuit layer 102. In an embodiment, the bottom substrate layer 12, the channel layer 14, the middle substrate layer 16, the adhesive layer 18, and the top substrate layer 20 may be bonded together to form inlet the port 24/mixing chamber 26, the capture port 28, the outlet port 30, and the fluid microchannel 34. The printed substrate layer 102 may include ink that is printed on a bottom surface of bottom substrate layer 12. Example dimensions of the layers of the test card 10, as well as methods of forming and bonding the layers, are described in more detail in U.S. application Ser. No. 15/185,661, entitled "Test Card for Assay and Method of Manufacturing Same", filed Jun. 27, 2016, which is hereby incorporated by reference and relied upon.

Figure 4A:
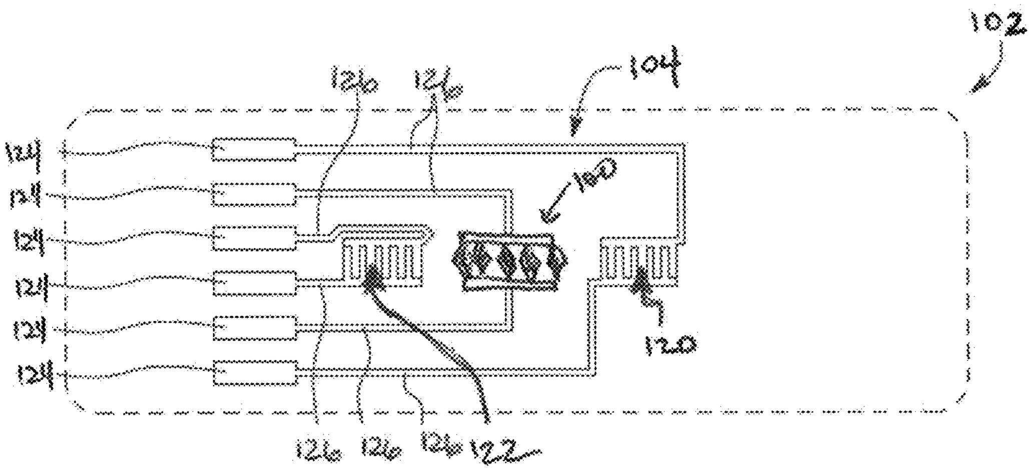
FIG. 4A is a top view of the printed circuit layer of the test card of FIG. 1 with dielectric ink omitted for clarity, according to an example embodiment of the present disclosure.
Figure 4B:
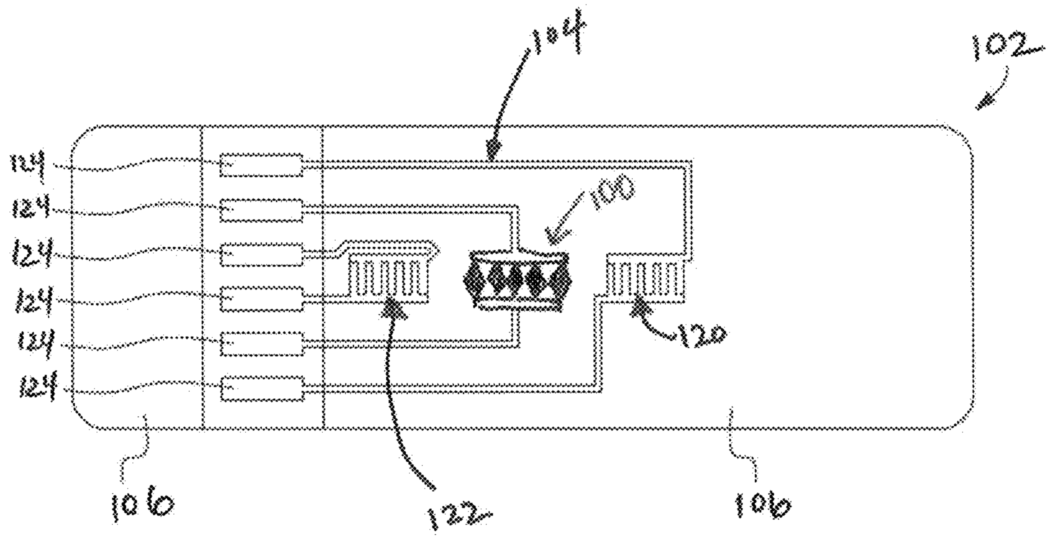
FIG. 4B is a top view of the printed circuit layer of the test card of FIG. 1 with dielectric ink shown, according to an example embodiment of the present disclosure.
Figure 4C:
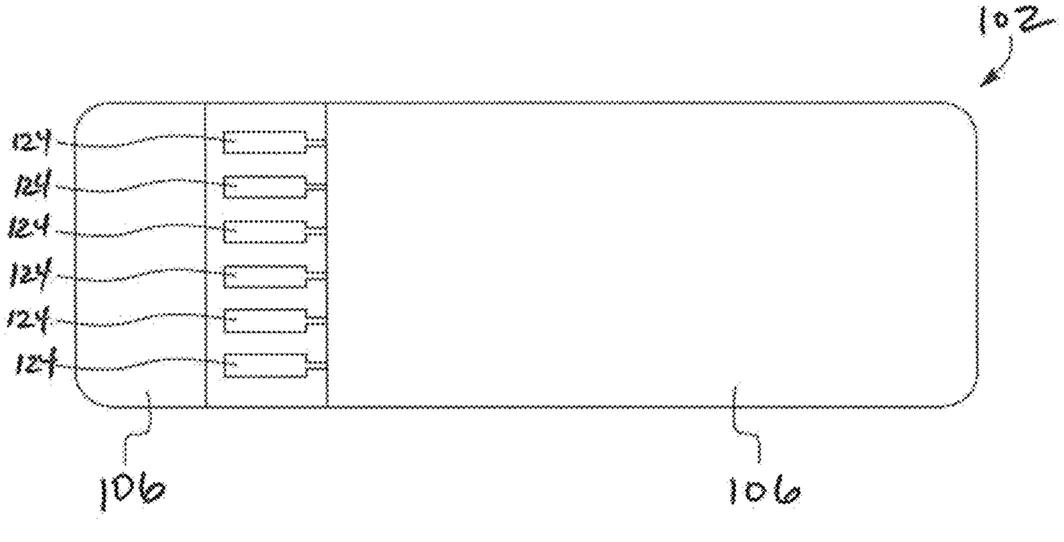
FIG. 4C is a bottom view of the printed circuit layer of the test card of FIG. 1 with dielectric ink shown, according to an example embodiment of the present disclosure.

FIGS. 4A and 4B illustrate a top view of a printing arrangement of the printed substrate layer 102, while FIG. 4C illustrates a bottom view of the same printing arrangement of the printed substrate layer 102. In FIG. 4A, only conductive ink 104 is shown, and dielectric ink 106 has been omitted for simplicity. FIG. 4B shows the top view of FIG. 4A with dielectric ink 106 underneath conductive ink 104. FIG. 4C illustrates a bottom view of a printing arrangement of the printed substrate layer 102, with dielectric ink 104 printed over conductive ink 106.

In the illustrated embodiment, the printed substrate layer 102 is printed onto the bottom surface of bottom substrate layer 12, before or after the bottom substrate layer 12 is bonded to one or more of channel layer 14, middle substrate layer 16, adhesive layer 18, and top substrate layer 20. As illustrated, the printed substrate layer 102 may be printed with a conductive ink 104 and a dielectric ink 106. The conductive ink 104 forms the electrical components of test card 10, whereas the dielectric ink 106 serve as protective, non-conductive coating to encapsulate the electrical components. The conductive ink 104 may become the electrical components once it is cured, for example, by heat or ultraviolet light. In an embodiment, one or more layers of conductive ink 104 is printed and then cured, and then one or more layers of dielectric ink 106 is printed and cured. In another embodiment, both the conductive ink 104 and the dielectric ink 106 are printed, and then both the conductive ink 104 and the dielectric ink 106 are cured. In another embodiment, several alternating layers of conductive ink 104 and dielectric ink 106 are printed to create multiple levels of conductive elements.

In an embodiment, the printed circuit layer 102 is screen printed on the bottom surface of bottom substrate layer 12 through a screen made of a stainless steel or a polymer mesh. A hardened emulsion can be used to block out all areas of the screen except for the desired print pattern for the conductive ink 104 and/or dielectric ink 106, so that the conductive ink 104 and/or dielectric ink 106 is pushed through the screen in the desired print pattern.

In the illustrated embodiment, the conductive ink 104 is printed to form a heater 100, as well as electrodes 120, 122 upstream and downstream of the heater 100 along microchannel 34. The conductive ink 104 may also form electrodes 124, which receive current from an analyzer device for controlling activation of the electrodes 120, 122 and the heater 100. The conductive ink 104 may further form electrical lines 126 connecting the electrodes 124 with the electrodes 120, 122 and/or the heater 100. The electrodes 120 and the electrodes 122 may be used to determine whether a fluid sample has flowed through fluid microchannel 34 so that the heater 100 may be used to heat the fluid to cause a PCR within the microchannel. In an embodiment, the electrodes 120, 122 utilize a changing dielectric constant as fluid flows through microchannel 34 to determine whether fluid has flowed therethrough, as the dielectric constant differs considerably when there is liquid in the microchannel at the electrodes 120, 122. Test card 10 also includes screen printed electrodes 124, which are in electrical communication with heater 100 and electrodes 120,122 via electrical lines 126. By placing a current source (from the analyzer device) in conductive communication with the electrodes 124, the current source can activate heater 100 and/or electrodes 120,122.

As illustrated in FIG. 4C, dielectric ink 106 has been printed over the majority of the electrical components formed by conductive ink 104. The dielectric ink 106 serves as protective, non-conductive coating to encapsulate the electrical components. In the illustrated embodiment, the only electrical components visible from the bottom of test card 10 are electrodes 124 because the electrodes 124 are the only electrical components intended to contact corresponding electrodes or contacts of an outside source of current (e.g., an analyzer device). By applying current from the outside source to the electrodes 124, all other electrical components of the test card 10 can be powered and controlled. As illustrated, the electrodes 124 can be separated from each other (e.g., not be electrically connected to each other on the test card 10) so that each of the heater 100 and the electrodes 120,122 can be controlled independently of each other.

Figure 5:
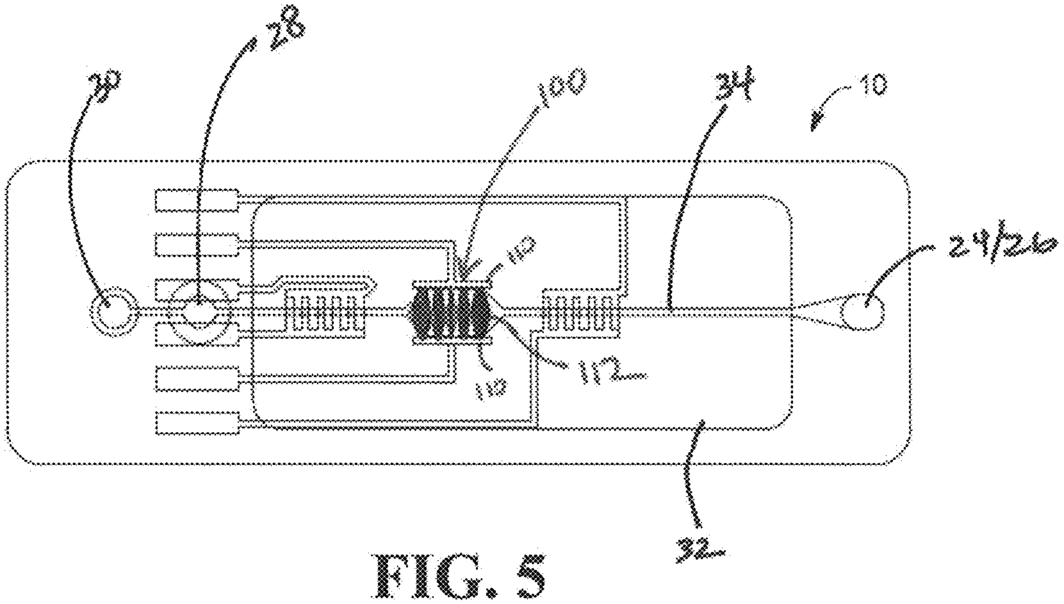
FIG. 5 is a top view of the test card of FIG. 1 in which certain layers are shows as being transparent to show the printed circuit layer, where dielectric ink on a bottom of the test card has been omitted for clarity, according to an example embodiment of the present disclosure.

FIG. 5 shows a top view of a fully assembled test card 10. Because the bottom substrate layer 12, channel layer 14, middle substrate layer 16, adhesive layer 18, and top substrate layer 20 are transparent in the illustrated embodiment, the printed circuit layer 102 is visible from the top view. In FIG. 5, the dielectric ink 106 on the bottom of test card 10 has been omitted for simplicity.

Figure 6:
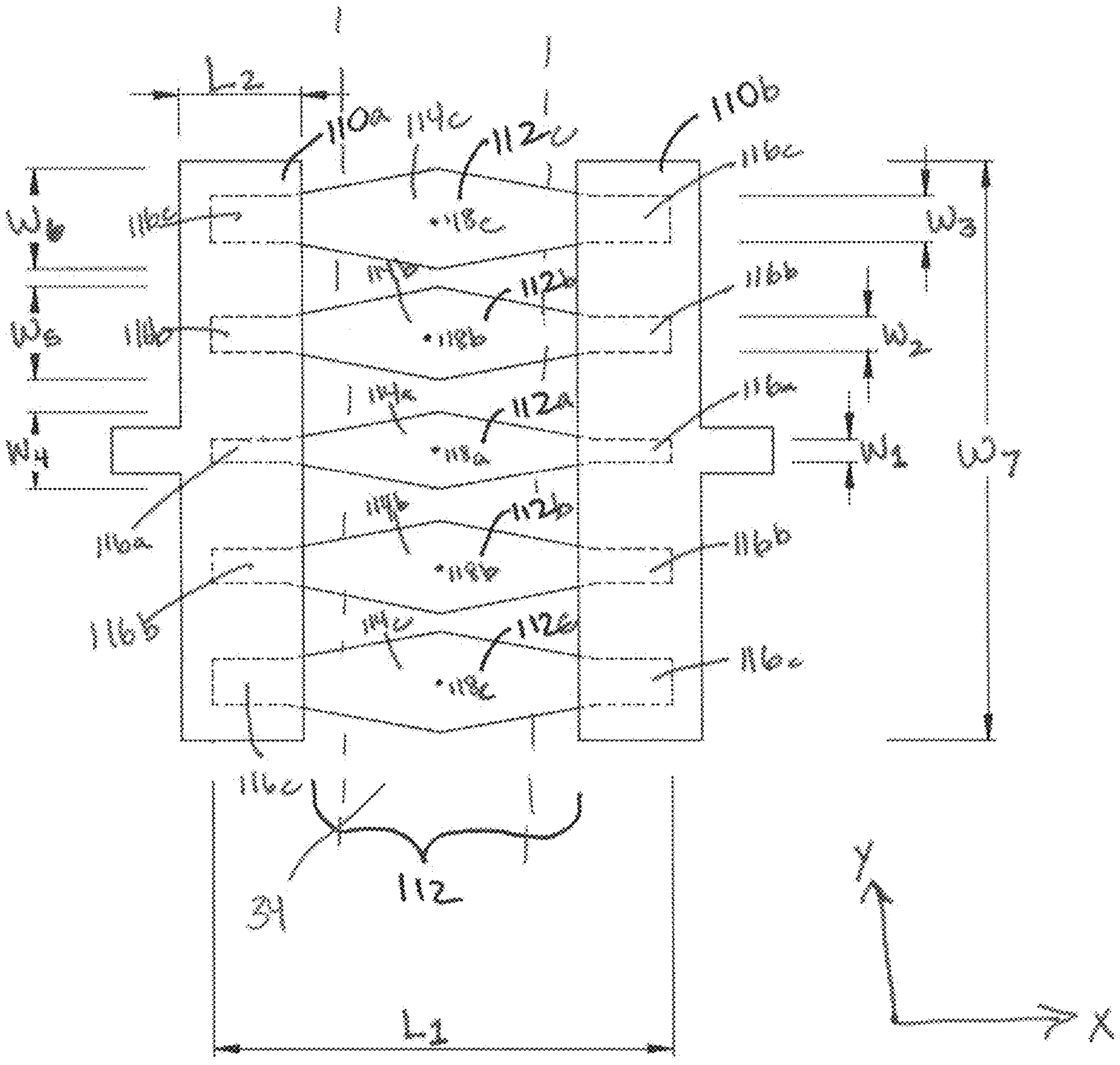
FIG. 6 is a detailed view of an example embodiment of a heater, according to an example embodiment of the present disclosure.

FIG. 5 illustrates the alignment of the heater 100 on printed circuit layer 102 in relation to fluid microchannel 34, while FIG. 6 illustrates a detailed view of the heater 100. In the illustrated embodiment, the heater 100 includes two electrodes 110 electrically connected by a plurality of heater bars 112. As illustrated in FIG. 5, electrodes 110 are aligned on opposite sides of the microchannel 34, with the plurality of heater bars 112 aligned so as to cross the microchannel 34 in a direction approximately perpendicular to the microchannel 34. By applying current to the electrodes 110, the fluid within the microchannel 34 may be heated by the heater bars 112 to cause a PCR. The disclosed heater 100 is therefore particularly useful in causing a PCR within a fluid microchannel due to the way that the electrodes 110 align on the sides of the microchannel and the heater bars 112 cross the microchannel. In FIG. 6, the microchannel 34 is shown in broken lines to illustrate this alignment.

In an embodiment, the electrodes 110 may be formed of silver ink, while the heater bars 112 may be formed of carbon ink. In an alternative embodiment, the electrodes 100 and the heater bars 112 may be formed of the same or a different material, for example, silver ink, carbon ink, another conductive ink, or another electrically conductive material besides a cured ink.

In the illustrated embodiment, the plurality of heater bars 112 includes a central heater bar 112*a*, first outer heater bars 112*b*, and second outer heater bars 112*c*. In the illustrated embodiment, each of central heater bar 112*a* and outer heater bars 112*b*, 112*c* is formed with a central diamond shape 114 (shown as 114*a*, 114*b*, 114*c*) and two protruding ends 116 (shown as 116*a*, 116*b*, 116*c*). The protruding ends 116 overlap with the electrodes 110 (shown as first electrode 110*a* and second electrode 110*b*) to place the electrodes 110 in electrical communication with each other. Although five heater bars 112 are shown in the illustrated embodiment, it should be understood by those of ordinary skill in the art that more or less heater bars may be used. The electrodes 110 may be printed either before or after the plurality of heater bars 112 so that the electrodes 110 and the plurality of heater bars 112 overlap.

Figure 9:
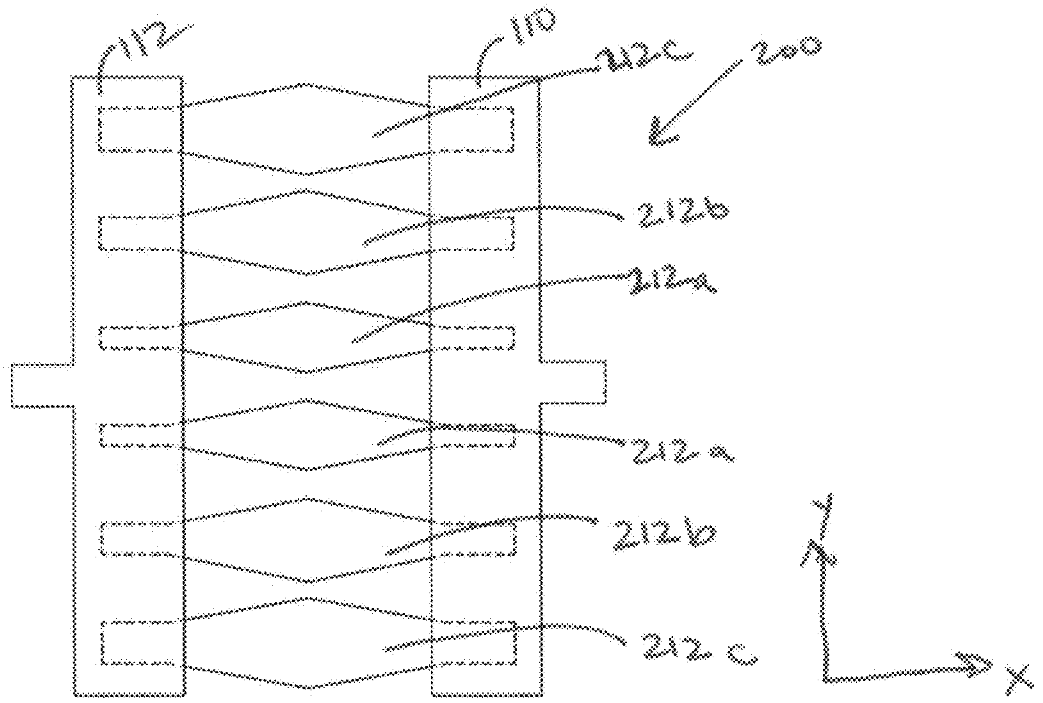
FIG. 9 shows a detailed view of an alternative example embodiment of a heater, according to an example embodiment of the present disclosure.
Figure 10:
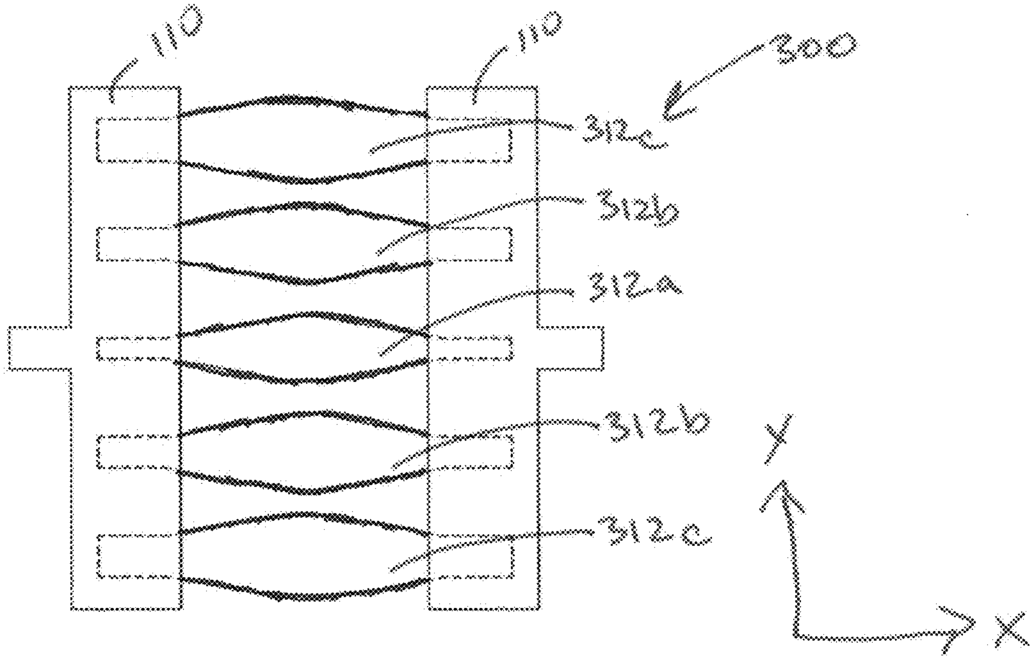
FIG. 10 shows a detailed view of another alternative example embodiment of a heater, according to an example embodiment of the present disclosure.
Figure 11:
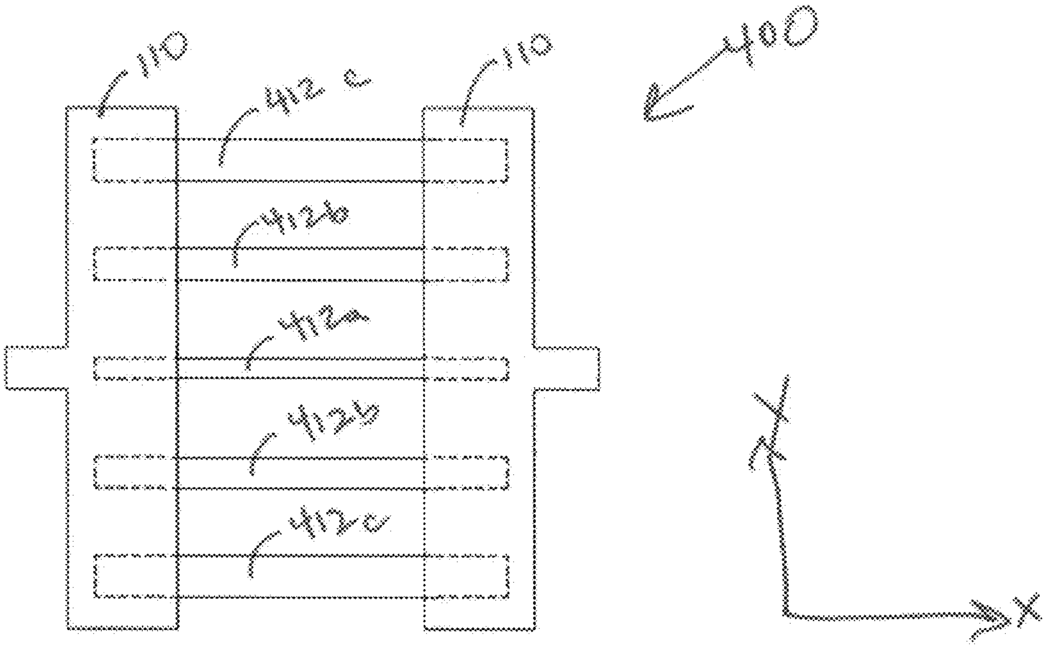
FIG. 11 shows a detailed view of another alternative example embodiment of a heater, according to an example embodiment of the present disclosure.

In the illustrated embodiment, each of the plurality of heater bars 112 increases in width in the y-direction from first electrode 110*a* to a central point 118 (shown as 118*a*, 118*b*, 118*c*) and then decreases in width in the y-direction from the central point 118 to second electrode 110*b*, creating a diamond shape with a largest width in the y-direction at central point 118. It is envisioned that other shapes could be used, for example, an oval shape that omits the sharp points at central point 118 but maintains a largest width at central point 118. Example embodiments of other shapes are illustrated at FIGS. 9 to 11.

In the illustrated embodiment, central heater bar 112*a* is thinner in the y-direction than outer heater bars 112*b*, 112*c*, giving central heater bar 112*a* a higher resistance than the outer heater bars 112*b*, 112*c*. As illustrated, the central heater bar 112*a* is thinner in the y-direction at central point 118*a* of the diamond shape and also at each protruding end 116*a* than outer heater bars 112*b*, 112*c* at 118*b*, 118*c* and 116*b*, 116*c*, respectively.

In an embodiment, the width $W_1$ of protruding ends 116*a* of central heater bar 112*a* in the y-direction may be about 0.30 mm, the width $W_2$ of protruding ends 116*b* of outer heater bars 112*b* in the y-direction may be about 0.45 mm, and the width $W_3$ of protruding ends 116*c* of outer heater bars 112*c* in the y-direction may be about 0.60 mm. In another embodiment, $W_2$ may be any width greater than $W_1$, and $W_3$ may be any width greater than $W_2$. In another embodiment, $W_2$ may be about $1.5\times W_1$, and $W_3$ may be about $1.33\times W_2$ or about $2\times W_1$. In another embodiment, $W_2$ may be about $1\times$ to $2\times W_1$, and $W_3$ may be about $1\times$ to $2\times W_2$. Those of ordinary skill in the art will recognize that other dimensions are possible.

In an embodiment, the width $W_4$ of the diamond or other shape of central heater bar 112*a* at central point 118*a* in the y-direction may be about 1.00 mm, the width $W_5$ of the diamond or other shape of outer heater bars 112*b* at central point 118*b* in the y-direction may be about 1.20 mm, and the width $W_6$ of the diamond or other shape of outer heater bars 112*c* at central point 118*c* in the y-direction may be about 1.30 mm. In another embodiment, $W_5$ may be any width greater than $W_4$, and $W_6$ may be any width greater than $W_5$. In another embodiment, $W_5$ may be about $1.2\times W_4$, and $W_6$ may be about $1.1\times W_5$ or about $1.3\times W_4$. In another embodiment, $W_5$ may be about $1\times$ to $2\times W_4$, $1\times$ to $1.5\times W_4$ or $1.1\times$ to $1.3\times W_4$, while $W_6$ may be about $1\times$ to $2\times W_5$, $1\times$ to $1.5\times W_5$ or $1\times$ to $1.3\times W_5$. Those of ordinary skill in the art will recognize that other dimensions are possible.

In an embodiment, each of the heater bars 112 may have a same length $L_1$ in the x-direction. For example, $L_1$ may be 6.00 mm. In an embodiment, the length $L_2$ of each electrode 110 in the x-direction may be about 1.60 mm, and the width $W_7$ of each electrode 110 in the y-direction may be about 7.50 mm.

As further illustrated, the width of the outer heater bars 112*b*, 112*c* in the y-direction at central points 118*b*, 118*c* and protruding ends 116*b*, 116*c* progressively increases as the distance from central heater bar 112*a* increases in the y-direction. That is, the width of outer bars 112*b* in the y-direction at central point 118*b* and/or protruding end 116*b* is greater than the width of central bar 112*a* in the y-direction at central point 118*a* and/or protruding end 116*a*, respectively. Likewise, the width of outer bars 112*c* in the y-direction at central point 118*c* and/or protruding end 116*c* is greater than the width of outer bars 112*b* in the y-direction at central point 118*b* and/or protruding ends 116*b*, respectively.

By using a heater with the same or similar structure as shown in FIG. 6, it has been determined that the electrical path between electrodes 110 can be controlled to ensure constant heater uniformity. Additionally, the disclosed heater uses lower power consumption than alternatives because of a lower total resistance. These advantages are illustrated for example, at FIGS. 7A to 7C and 8A to 8C.

Figure 7A:
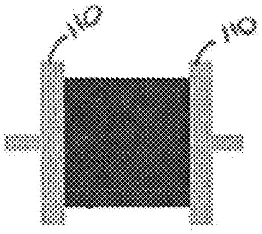
FIGS. 7A to 7C show an example of the current density and temperature associated with an alternative heater design, according to an example embodiment of the present disclosure.
Figure 7B:
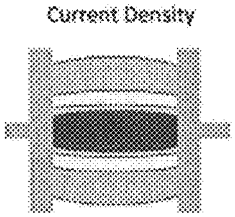
Figure 7C:
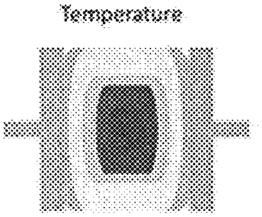

FIGS. 7A to 7C show a heater design in which a large square heater bar is placed between two electrodes 110. In the illustration, the large square has a 6 mm square area. FIG. 7B shows a current density of the square heater bar of FIG. 7A, while FIG. 7C shows the temperature profile. With the heater shown, electricity passes through electrodes 110. Once the current passes through electrodes 110 into a central region, the path of least resistance for the current is to flow through the center of the central region. As shown in FIG. 7B, the current density is highest in the center of the central region because this region is the path of least resistance for the current. As shown in FIG. 7C, the resultant temperature distribution is uneven because the current is maximum in the center and dramatically drops (e.g., up to 20 degrees) around the edges. Thus, with the design of FIG. 7A, neither the current nor the temperature is uniformly distributed, with the non-uniform current density resulting in the uneven temperature distribution. The large temperature gradient may cause major issues for assays such as PCR, which require precise temperature control.

Figure 8A:
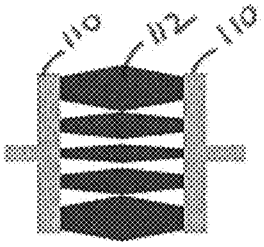
FIGS. 8A to 8C show an example of the current density and temperature associated with an example embodiment of a heater design, according to an example embodiment of the present disclosure.
Figure 8B:
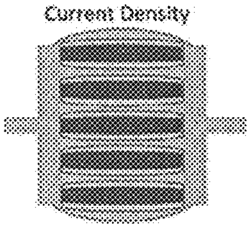
Figure 8C:
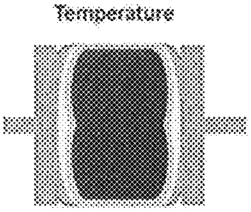

In contrast, FIGS. 8A to 8C show the effects of the presently disclosed heater 100 design. FIG. 8A again illustrates the presently disclosed design using progressively thickening heater bars. FIG. 8B shows the current density, while FIG. 8C shows the temperature profile. As illustrated, by varying the heater size/resistance in the y-direction, current is forced to travel further from the centerline in the y-direction of the heater. Additionally, the variation in heater dimensions along the x-axis forces maximum current density nearer the electrodes 110. As shown in FIG. 8C, the temperature is substantially uniform, thereby providing precise temperature control for a PCR on the test card 10.

It should be understood that the disclosed heater design may be utilized with other materials besides cured conductive inks. For example, another conductive material such as a metal may be sized and/or shaped as shown to achieve the same advantages.

FIG. 9 illustrates an alternative embodiment of a heater 200 according to the present disclosure. FIG. 9 differs from FIG. 6 in that heater 200 includes two central heater bars 212*a* between outer heater bars 212*b*, 212*c*, whereas heater 100 only shows one central heater bar 112*a* between outer heater bars 112*b*, 112*c*. Thus, FIG. 9 illustrates that the number of particular heater bars 112, 212 may vary from embodiment to embodiment, and that increasing the number of any particular size or location of a heater bar 112, 212 is within the scope of the present disclosure. It should also be understood to those of ordinary skill in the art that the materials, dimensions and other elements described above with respect to heater 100 are equally applicable to heater 200.

FIG. 10 illustrates an alternative embodiment of a heater 300 according to the present disclosure. FIG. 10 differs from FIG. 6 in that heater 300 includes rounded heater bars 312*a*, 312*b*, 312*c* as opposed to the diamond-shaped heater bars of heater 100. Despite this difference, heater 300 maintains the progressively-increasing width of heater 100, where the outer heater bars 312*b* are wider than the central heater bar 312*a* in the y-direction at the central point between electrodes and at the protruding ends, and the outer heater bars 312*c* are wider than outer heater bars 312*b* at the central point between electrodes and at the protruding ends. It should be understood by those of ordinary skill in the art that other shapes can also be used in place of the diamond shape of heater 100. It should also be understood to those of ordinary skill in the art that the materials, dimensions and other elements described above with respect to heater 100 are equally applicable to heater 300.

FIG. 11 illustrates an alternative embodiment of a heater 400 according to the present disclosure. FIG. 11 differs from FIG. 6 in that heater 400 includes straight heater bars 412*a*, 412*b*, 412*c* as opposed to the diamond-shaped heater bars of heater 100. Despite this difference, the heater 400 maintains the progressively-increasing width of heater 100. In this example, the outer heater bars 412*b* are wider than central heater bar 412*a* in the y-direction at the central point between electrodes and at the protruding ends, and the outer heater bars 412*c* are wider than outer heater bars 412*b* at the central point between electrodes and at the protruding ends. Although the heater 400 may not function as uniformly as heater 100, it is contemplated that heater 400 could still be advantageous over, for example, the heater illustrated at FIGS. 7A to 7C. It should also be understood to those of ordinary skill in the art that the materials, dimensions and other elements described above with respect to heater 100 are equally applicable to heater 400.

In the illustrated embodiments, the plurality of heater bars 112 are printed with the same type of conductive ink and in the same general shape, and the size of the plurality of heater bars is used to cause the central heater bar 112*a* to have the greatest resistance, with the resistance of the outer heater bars 112*b*, 112*c* progressively decreasing as the distance from central heater bar 112*a* increases. That is, central heater bar 112*a* has the greatest resistance, first outer heater bars 112*b* have less resistance than central heater bar 112*a*, and second outer heater bars 112*c* have less resistance that first outer heater bars 112*b*. It is also envisioned, however, that the size of heater bars 112*a*, 112*b*, 112*c* may be the same or similar, and the overall shape or materials for each heater bar may be altered so that central heater bar 112*a* has the greatest resistance, first outer heater bars 112*b* have less resistance that central heater bar 112*a*, and second outer heater bars 112*c* have less resistance that first outer heater bars 112*b*. For example, the shape of all heater bars could be the same or similar, and the material used for central heater bar 112*a* could cause central heater bar 112*a* to have the greatest resistance, the material used for first outer heater bars 112*b* could cause first outer heater bars 112*b* to have less resistance than central heater bar 112*a*, and the material used for second outer heater bars 112*c* could cause second outer heater bars 112*c* to have less resistance that first outer heater bars 112*b*.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. A test card for analyzing a fluid sample, comprising:

at least one substrate layer including a microchannel extending through at least a portion of one of the substrate layers; and a printed substrate layer that is bonded to or printed on one substrate layer of the at least one substrate layer, the printed substrate layer including a heater printed on the printed substrate layer so as to align with at least a portion of the microchannel, the heater including:

two electrodes aligned on opposite sides of the microchannel; and a plurality of heater bars electrically connecting the two electrodes, the plurality of heater bars including a central heater bar disposed between outer heater bars, wherein the central heater bar is thinner than the outer heater bars in a direction approximately parallel to the microchannel.

2. The test card of claim 1, wherein the at least one substrate layer includes a plurality of bonded layers.

3. The test card of claim 1, wherein the electrodes are printed onto the printed substrate layer with a silver ink.

4. The test card of claim 1, wherein the plurality of heater bars is printed onto the printed substrate layer with a carbon ink.

5. The test card of claim 1, wherein the plurality of heater bars includes the central heater bar, a pair of first outer heater bars, and a pair of second outer heater bars, wherein the central heater bar is disposed between the first outer heater bars, wherein the first outer heater bars are disposed between the second outer heater bars, wherein the central heater bar is thinner than the first outer heater bars in the direction approximately parallel to the microchannel, and wherein the first outer heater bars are thinner than the second outer heater bars in the direction approximately parallel to the microchannel.

6. The test card of claim 1, wherein the central heater bar is thinner than the outer heater bars at a central point between the two electrodes.

7. The test card of claim 1, wherein the central heater bar is thinner than the outer heater bars at respective points of contact with at least one of the two electrodes.

8. The test card of claim 1, wherein the central heater bar is thinner than the outer heater bars at respective portions aligned with the microchannel.

9. The test card of claim 1, wherein the plurality of heater bars each includes a central diamond shape and two protruding ends, wherein the protruding ends overlap with the two electrodes to place the two electrodes in electrical communication with each other.

10. The test card of claim 1, wherein the central heater bar includes two or more central heater bars.

* * * * *